United States Patent [19]

Raftopoulos et al.

[11] Patent Number: 4,854,312
[45] Date of Patent: Aug. 8, 1989

[54] EXPANDING INTRAMEDULLARY NAIL

[75] Inventors: Demetrios D. Raftopoulos, Ida, Mich.; James D. Baril, Toledo, Ohio

[73] Assignee: The University of Toledo, Toledo, Ohio

[21] Appl. No.: 181,117

[22] Filed: Apr. 13, 1988

[51] Int. Cl.[4] .............................................. A61F 5/04
[52] U.S. Cl. .......................... 128/92 YY; 128/92 YW
[58] Field of Search ....... 128/92 YY, 92 YK, 92 YW, 128/92 YV, 92 YT, 92 YS

[56] References Cited

U.S. PATENT DOCUMENTS

| 2,327,434 | 8/1943 | Johnston | 128/92 YW |
| 2,490,364 | 12/1949 | Livingston | 128/92 YK |
| 2,998,007 | 8/1961 | Herzog | 128/92 YY |
| 3,530,854 | 9/1970 | Kearney | 128/92 YK |
| 3,678,925 | 7/1972 | Fischer et al. | 128/92 YW |
| 3,716,051 | 2/1973 | Fischer | 128/92 YW |
| 3,760,802 | 9/1973 | Fischer et al. | 128/92 YY |
| 4,091,806 | 5/1978 | Aginsky | 128/92 YY |

FOREIGN PATENT DOCUMENTS 742097 10/1943 Fed. Rep. of Germany ........ 128/92 YY

Primary Examiner—Robert A. Hafer
Assistant Examiner—Michael Brown
Attorney, Agent, or Firm—Vincent L. Barker, Jr.

[57] ABSTRACT

An intramedullary nail for the fixation of bone fractures is formed of two slidably engaging elongate members. One of the members includes an articulated channel which serves to bend the other member to form an expanding end region within the bone cavity to achieve fixation therein.

7 Claims, 2 Drawing Sheets

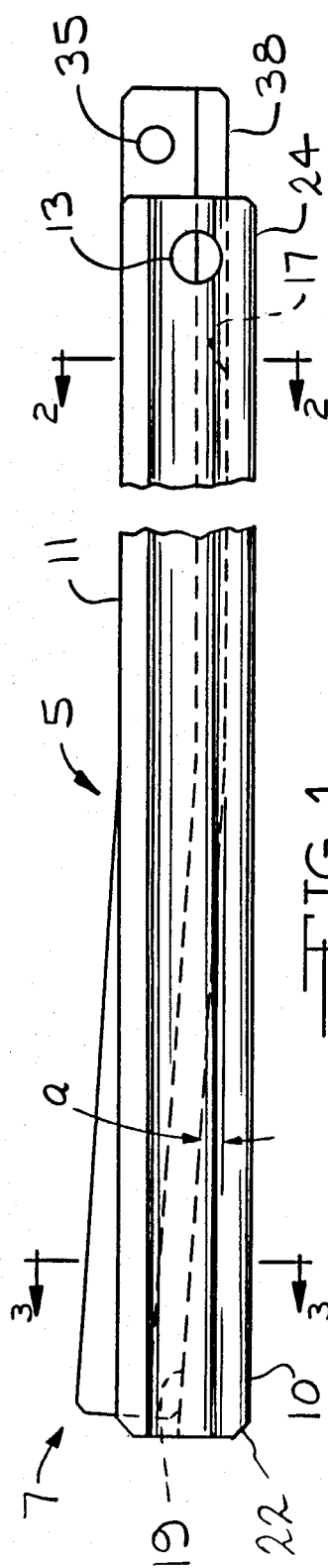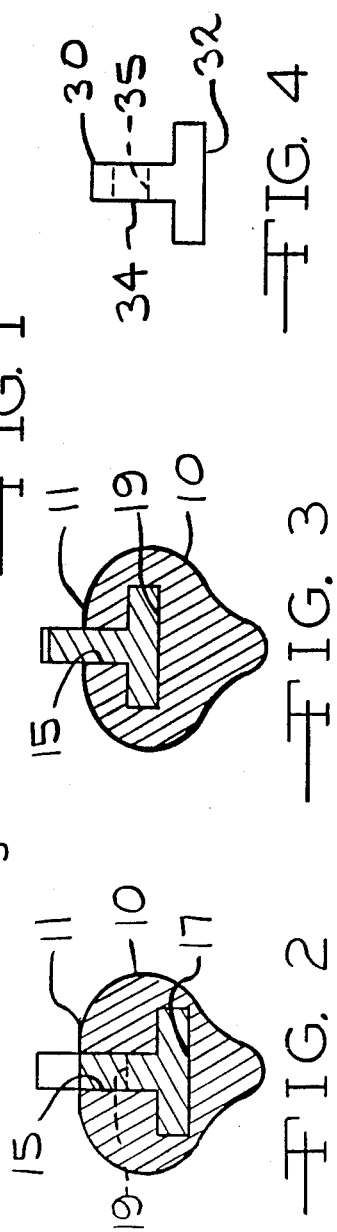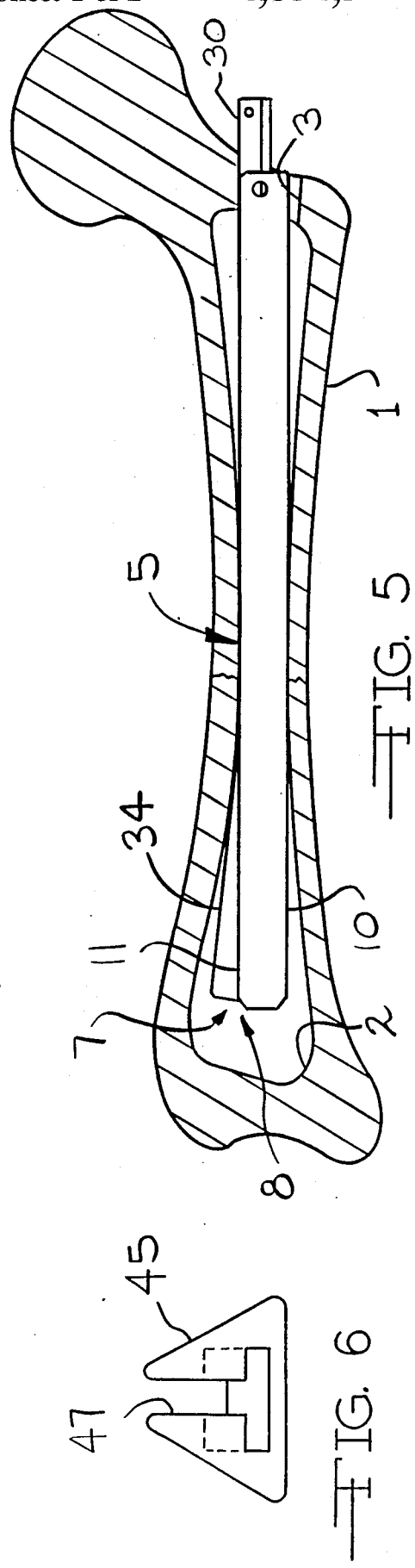

EXPANDING INTRAMEDULLARY NAIL

TECHNICAL FIELD

The invention disclosed herein relates to intramedullary nails for the fixation of bone fractures wherein the nail has an expandable or divergent section for securely maintaining the nail within the medullary cavity of at least one of the fractured bone portions.

BACKGROUND

The use of an intramedullary nail for the fixation of bone fractures is well known. Such a device rejoins and reinforces the broken bone portions of a body limb and, in many instances, permits the functional rehabilitation of the limb within a relatively short time.

The earliest types of intramedullary nails consisted of a single diameter rod constructed of a non-corrosive material. Typically, the diameter of the nail was selected to correspond with the narrowest part of the medullary cavity of the bone into which the nail was to be inserted. In order to use an intramedullary nail in fractures which occur in areas of the femur proximal or distal from the narrowest area of the intramedullary canal, it is necessary to use a larger diameter nail.

The use of a larger diameter nail was made possible by enlarging the medullary cavity by reaming the bone. Typically, such a nail was constructed with a uniform cross-section throughout its entire length except for the front tip which was tapered inwardly to assist in the insertion of the nail through the bone marrow. However, the principal drawback of this type of nail is that the practice of enlarging the medullary cavity tends to weaken the shaft of the bone and reduce the blood supply to the fractured ends, thereby impeding the healing process.

Another problem associated with the above-described intramedullary nails is that, in some instances, the lateral support provided by the nail is very limited due to the configuration of tubular bones. Typically, tubular bones have a longitudinal extending, marrow-containing cavity having a contour which converges in the central portion of the bone and then diverges in a longitudinal direction near the ends of the bone. Consequently, an intramedullary nail having a uniform cross-section will typically only contact the inner wall of the medullary cavity of the bone only over a small region. Such a nail provides only limited lateral support between the fractured bone portions.

One approach to providing increased lateral support at the fracture was to use an intramedullary nail having an expandable end portion. Such a nail has a retracted diameter in the end portion which permits the nail to be inserted through the convergent portion of the medullary cavity, and thereafter expanded to enlarge the increased diameter inner wall of the divergent portion. Such expansion nails have resulted in increased lateral retention of the fractured bone portion but are relatively expensive and sometimes require complex devices to effect the expansion of the end portion. Typical examples of such prior art expandable nails are shown in U.S. Pat. Nos. 3,759,257, 3,760,802, 3,779,239, 3,530,854 and 4,091,806.

The present invention provides a strikingly simple solution, to problems presented by fractured bones.

DISCLOSURE OF THE INVENTION

This invention pertains to a fixation device for insertion into a medullary cavity of a bone comprising a first elongate member having a non-straight or articulated channel extending along the length thereof; and a second elongate member adapted to be slidably positioned in the channel of the first member, the first and second members and channel being configured such that at a distal region of the device the first and second members form a divergent section to substantially fix the device within the cavity of the base.

BRIEF DESCRIPTION OF THE DRAWINGS

FIG. 1 is a side view of a fixation device or intramedullary nail according to the principles of this invention;

FIG. 2 is a cross-sectional view of the first or main member shown in FIG. 1 taken along view 2—2;

FIG. 3 is a cross-sectional view of the main member shown in FIG. 1 taken along view 3—3;

FIG. 4 is an end view of the second member shown in FIG. 1;

FIG. 5 is a side view similar to FIG. 1 but showing the nail in an expanded position located within the medullary cavity of a fractured bone;

FIG. 6 is an end view of a main member having an alternative triangular cross-sectional shape;

BEST MODE OF CARRYING OUT THE INVENTION

Figure 7:
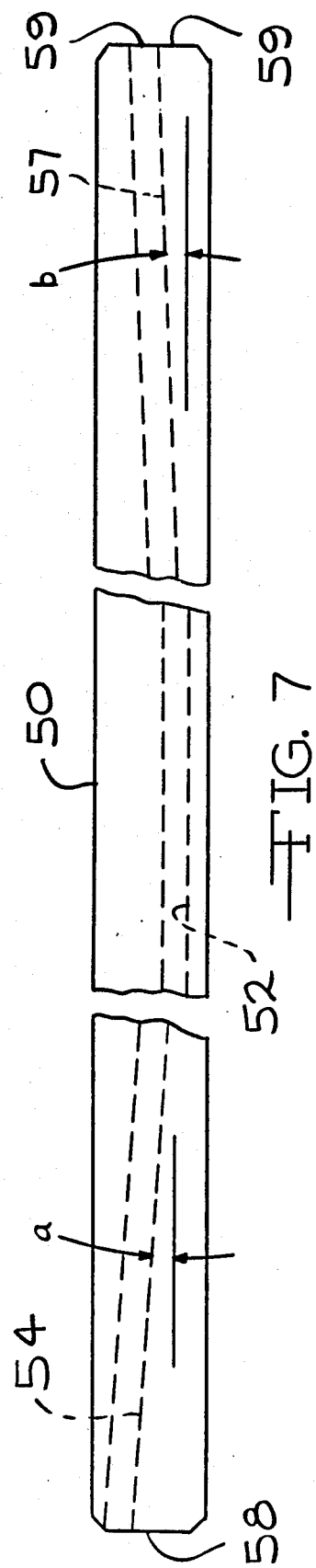
FIG. 7 is a side view of a main member of generally rectangular cross-section having a channel having two inclined regions to provide a nail having two divergent sections, one at each end.
Figure 8:
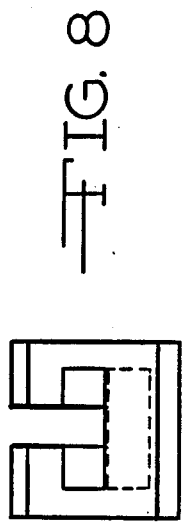
FIG. 8 is an end view of the main member shown in FIG. 7.

As shown in FIG. 1, the present invention is comprised of two elongated members. Compared to previous expanding fixation devices, the present invention is incredibly simple. Fixation device 5 is comprised of first elongate member 10 and second elongate member 30. As can be seen in FIGS. 1, 2 and 3, first or main elongate member 10 is generally irregular in cross-section and includes an articulated channel 15 extending along the length thereof, that is, from first end 22 to opposite end 24. Channel 15, as shown here, is comprised of a first or base section 17 and a second or ramp section 19. Base section 17 is substantially straight and parallel to the longitudinal axis of first member 10. Second or ramp section 19, desirably, has an arcuate configuration. That is, ramp section gently curves upwardly towards upper surface 11 of member 10. Further, it is desirable that the base section 17 extend approximately ⅔ of the length of first member 10. That is, ramp section 19 occupies approximately ⅓ of the length of member 10 from end 22.

To facilitate extraction of main member 10, an aperture 13 is positioned in member 10 near end 24 to permit first member 10 to be grasped by, for example, a hooked implement by which member 10 can be pulled from the bone after healing.

As shown in FIG. 4, second or slide member 30 is a T-shaped elongate member having a foot section 32 and an extension 34 extending laterally therefrom. Prior to insertion, second member 30 is substantially straight.

The inclined portion of channel 15 deflects or bends second member 30 upon insertion into first member 10.

Also to facilitate removal, second member 30 incorporates an aperture 35 at end 38 of member 30 to permit second member, 30 to be engaged by a hooked removal tool to pull member 30 from first member 10 while located within the bone after healing.

First and second members 10 and 30 may be constructed of any suitable non-corrosive biocompatible alloy such as stainless steel, for example. The types of steel are selected from known steels having the desired properties of strength, modules of flexure and biocompatibility, etc.

As shown in FIG. 5, the fixation device or nail 5 of this invention is positioned within cavity 2 of bone 1. Intramedullary nails are generally implanted in either of two ways. The first method consists of making an incision over the fracture site, exposing the fracture, reducing the fracture, then through a second incision, inserting the rod through the end of the bone. The second technique is to reduce the fracture under radiographic control on a special operating table. Similarly, once the fracture is reduced, the guide pin is inserted through an end of the bone across the fracture site. The present fixation device may be inserted in the bone by any suitable technique.

As such, after reducing the fracture, first or main elongate member 10 is inserted into the medullary cavity 2 of bone 1 through an opening 3 formed in bone 1. Generally, a passageway is drilled or reamed in the soft or porous bone occupying cavity 2 as is known in the art. With first or main member 10 properly positioned in cavity 2, second member 30 is inserted into channel 15 of first member 10 and slid along the length thereof to the desired position. As the forward end 36 of second member 5 is slid along second or ramp section 19 of first member 10, the forward portion of extension 34 is forced or moved laterally beyond upper surface 11 of first member 10 to form a divergent section 8 at the forward or distal region 7 of device 5. Thus, the device effectively fixes the distal fragment of the bone and impedes relative rotation between the bone fragments. Thus, simple as well as comminuted fractures, including fractures which occur proximal or distal to the narrow region of the bone, can be readily fixed.

As shown in Figure 1, extension 34 of second member 30 is located at or slightly beneath the upper surface 11 of first member 10 along the base section 17 of channel 15. However, it is to be understood that other configurations may also be acceptable. For example, extension 34 may slightly extend beyond upper surface 11 over substantially the entire length, if desired.

As shown in FIG. 6, main member 45 of that embodiment has a triangular cross-sectional shape with channel 47 extending along the length thereof. Any suitable cross-sectional shape may be employed for main member 45 but the irregular or "cloverleaf" type of FIGS. 1-3 has been found to be particularly effective in preventing relative rotation of bone sections.

In some instances, it may be desirable to have a fixation device wherein both ends of a fixation device have a divergent section. According to the principles of this invention, this may be readily accomplished by incorporating a plurality of ramp sections in the channel extending along the length thereof, one at each end. As shown in FIG. 7, first or main member 50 has a channel 51 extending along the length thereof. Base section 52 of channel 51, which is substantially straight, is located intermediate a first ramp section 54 and a second ramp section 57. First ramp section 54 is associated with forward or first end 58 of main member 45, and second ramp section 57 is associated with second end 59 of first member 50.

As shown, first ramp section 50, which is substantially straight, forms an angle A with respect to base section 52. Similarly, second ramp section 57, which is also substantially straight, forms an angle B with respect to base section 52. Angles "A" and "B" may be any suitable angle, and they may or may not be equal. Of course, the transition segments of the channel between ramp sections 54 and 57 and base should be of a suitably generous radius to facilitate the passage of the sliding member therethrough.

Figure 9:
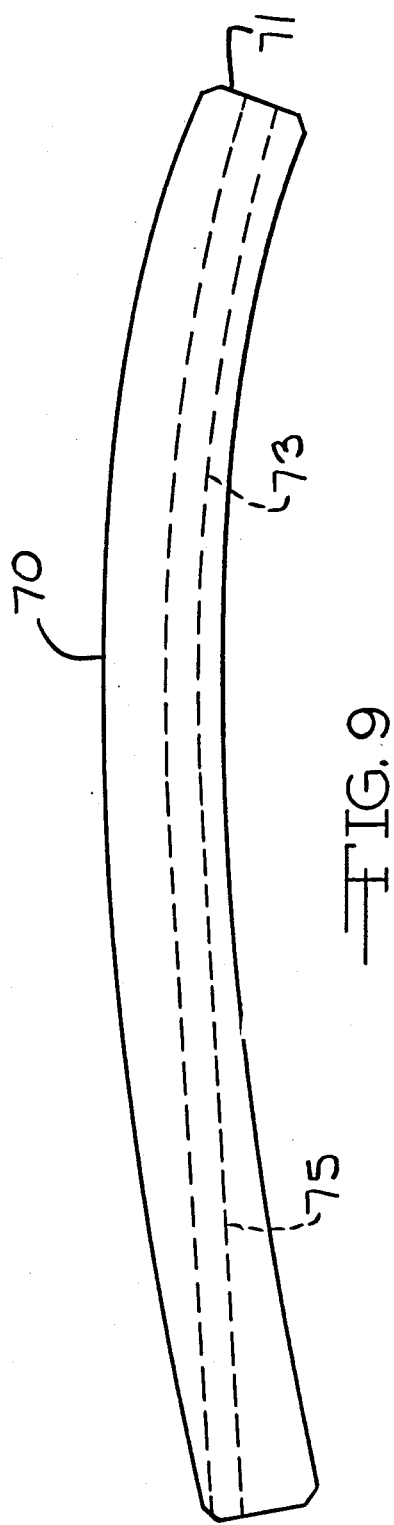
FIG. 9 is a side view of another alternative embodiment for the main member wherein the main member is curved to accommodate the curvature of the medullary cavity of the bone.

As shown in FIG. 9, main member 70 has an arcuate shape to generally form to the curvature of the outer layer of bone, generally defining the intramedullary cavity. Similarly, main member 70 has a non-straight or articulated channel 71 extending along the length thereof wherein the second section 75 is inclined or angled with respect to base section 73. Base section 73 and/or ramp section 75 may be configured as straight or arcuate as desired.

As shown and described thus far, the fixation device according to the principle for this invention is comprised of merely two parts. No fastening device or locking device, such as a set-screw, is generally necessary since the frictional force established between the first and second members due to the bowing of the second member in the articulated channel is believed to be sufficient to maintain the position between the first and second members, once properly installed within the bone.

It is apparent that within the scope of the present invention, modifications and different arrangements can be made other than is herein disclosed. The present disclosure is merely illustrated with the invention comprehending all variations thereof.

INDUSTRIAL APPLICABILITY

The invention described herein is readily applicable to the medical profession.

We claim:

1. A fixation device for insertion into a medullary cavity of a bone comprising:
   a first elongate member of generally irregular cross section and having an articulated channel therein that is T-shaped in cross section and extending the length of said member,
   said T-shaped channel including a substantially straight base section extending parallel to the longitudinal axis of said member over a substantial length of said member and a ramp section including an arcuate configuration at a distal end portion diverging laterally of said axis and disposed adjacent said base section,
   said channel including a slot opening on the surface of the first member which extends longitudinally along its surface a distance at least equal to the length of said ramp section,
   a second elongate member that is T-shaped in cross section and is slidingly engaged in said channel, said second member being substantially straight longitudinally, the distal end portion of the channel and said second member being divergent in their engagement in said distal end portion of the channel to extend the second member through said slot and fix the device within the cavity of the bone, said second member bowing in its sliding movement along said distal end portion of the channel, whereby the friction between them maintains the relative position between the first and second members.

2. The device of claim 1 wherein the channel of the first member is inclined along both end regions such that a divergent section is formed at each end region of the device.

3. The device of claim 1 wherein the channel is inclined along less than about ⅓ of the length of the first member.

4. The device of claim 1 wherein the inclined portion of the channel forms an acute angle relative to a base portion of the channel.

5. A friction device for insertion into a medullary cavity of bone comprising:
 a first elongate straight member of irregular cross-sectional shape and having a channel, T-shaped in cross section, extending along the length thereof, the channel having a substantially straight base section and a second section inclined from the base section and extending in the distal end portion of said member, said channel forming an open slot longitudinally along at least the distal end portion of said first member,
 a second elongate straight member adapted to be slidably positioned in the channel of the first member, said second member being bendable along its length and T-shaped in cross-section adapted for sliding engagement with said channel of the first member, the second section of the channel causing said second member to extend laterally through the slot of the first member at a distal region of the latter when the second member is positioned along the channel of said first member to bow the second member and project it laterally and externally of the first member, thereby fixing the device within the cavity of the bone.

6. The device of claim 5 wherein the second section of the channel arcuately proceeds from the base section.

7. The device of claim 6 wherein the second section of the channel is substantially straight over a majority of the length thereof.

* * * * *